United States Patent [19]

Cipolli et al.

[11] Patent Number: 5,182,388

[45] Date of Patent: Jan. 26, 1993

[54] SALTS OF TRIAZINIC COMPOUNDS WITH OXYGENATED ACIDS OF PHOSPHORUS

[75] Inventors: Roberto Cipolli, Novara; Roberto Oriani; Gilberto Nucida, both of Milan; Enrico Masarati, Piacenza, all of Italy

[73] Assignee: Ministero Dell' Universita' E Della Ricerca Scientifica E Tecnologica, Rome, Italy

[21] Appl. No.: 683,425

[22] Filed: Apr. 11, 1991

[30] Foreign Application Priority Data

Apr. 11, 1990 [IT] Italy .............................. 20007 A/90

[51] Int. Cl.$^5$ .......................................... C07D 251/02
[52] U.S. Cl. ................... 544/195; 544/113; 544/196; 544/198
[58] Field of Search ................ 544/113, 195, 196, 198

[56] References Cited

U.S. PATENT DOCUMENTS

| | | | |
|---|---|---|---|
| 3,296,265 | 1/1967 | Garner | 544/195 |
| 4,154,930 | 5/1979 | Halpern | 544/195 |
| 4,203,882 | 5/1980 | Bertelli et al. | 524/100 |
| 4,333,869 | 6/1982 | Marciandi et al. | 524/140 |
| 4,393,207 | 7/1983 | Hummerich et al. | 544/196 |
| 4,420,577 | 12/1983 | Bertelli et al. | 524/83 |
| 4,442,255 | 4/1984 | Marciandi et al. | 524/100 |
| 4,504,610 | 3/1985 | Fontanelli et al. | 524/100 |
| 4,879,327 | 11/1989 | Poisson et al. | 544/195 |

FOREIGN PATENT DOCUMENTS 0055216  5/1979  European Pat. Off. .

OTHER PUBLICATIONS

Chattha et al., Chemical Abstract, 97(10) #73971e, 1982.

*Primary Examiner*—Mukund J. Shah
*Assistant Examiner*—Y. N. Gupta
*Attorney, Agent, or Firm*—Stevens, Davis, Miller & Mosher

[57] ABSTRACT

Salts of triazinic compounds with oxygenated acids of phosphorus, of the general formula (I):

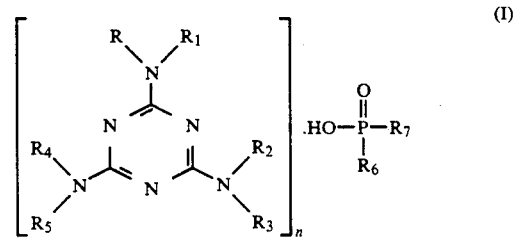

wherein:

at least one of radicals for R to $R_5$ is:

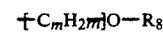

being:

m = an integer comprised between 2 and 8;
p = an integer comprised between 2 and 6;

The new salts having the general formula (I) are applied, in particular, as anti-flame additives for polymers.

4 Claims, No Drawings

SALTS OF TRIAZINIC COMPOUNDS WITH OXYGENATED ACIDS OF PHOSPHORUS

The present invention relates to new salts of triazinic compounds with oxygenated acids of phosphorus, which may be obtained by salifying derivatives of the 2,4,6-triamino-1,3,5-triazine with the acid containing phosphorus.

These salts are able to give the thermoplastic polymers or polymers showing elastomeric properties, particularly olefinic polymers or copolymers, high characteristics of self-extinguishing to flame.

In particular, object of the present invention are the salts of the general formula (I)

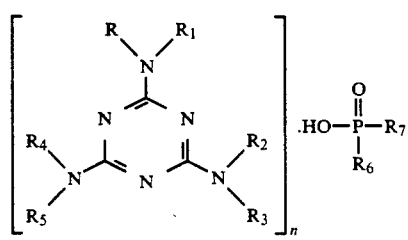

wherein:
at least one of radicals from R to $R_5$ is:

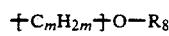

or

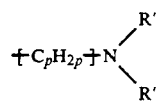

being:
m = an integer comprised between 2 and 8;
p = an integer comprised between 2 and 6;
$R_8$ = H; $C_1$-$C_8$ alkyl; $C_2$-$C_6$ alkenyl; $[-C_qH_{2q}-]O-R_9$, wherein
q is an integer comprised between 1 and 4 and
$R_9$ is hydrogen or $C_1$-$C_4$ alkyl; $C_6$-$C_{12}$ cycloalkyl or alkylcycloalkyl; radicals R', the same or different between them, are H; $C_1$-$C_8$ alkyl; $C_2$-$C_6$ alkenyl; $C_6$-$C_{12}$ cycloalkyl or alkylcycloalkyl; $C_1$-$C_4$ hydroxyalkyl with the provision that radicals $R_6$ and $R_7$, hereinafter described, are respectively different from H and OH; or the group;

is replaced by a heterocyclic radical bound to the alkyl chain through the nitrogen atom and optionally containing another heteroatom preferably selected from O, S, N; or in the formula (I) at least one of groups:

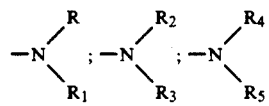

is replaced by a heteroyclic radical bound to the triazinic ring through the nitrogen atom and containing optionally another heteroatom preferably selected from O, S, N.

The other radicals from R to $R_5$, the same or different among them, have the above mentioned meaning or are: H; $C_1$-$C_{18}$ alkyl; $C_2$-$C_8$ alkenyl; $C_6$-$C_{16}$ cycloalkyl or alkylcycloalkyl, optionally substituted by hydroxyl or $C_1$-$C_4$ hydroxyalkyl function;

n is a number varying up to 6, in particular from 0.5 to 5;

$R_6$ is H; OH; —O—$C_1$—$C_8$ alkyl; —O—aryl, optionally substituted by a $C_1$-$C_8$ alkyl; aralkyl, optionally substituted by a $C_1$-$C_4$ alkyl; $C_1$-$C_4$ alkyl, optionally substituted by a carboxylic group; aryl;

$R_7$ is H; OH; —O—$C_1$—$C_8$ alkyl; —O—aryl; $C_1$-$C_4$ alkyl; aryl; furthermore, $R_7$ is;

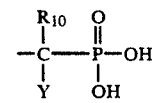

wherein $R_{10}$ is hydrogen or $C_1$-$C_{12}$ alkyl and Y is OH or $R_{10}$;

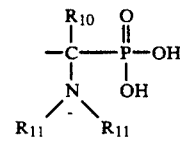

wherein $R_{10}$ has the previously specified meaning and radicals $R_{11}$, the same or different between them, are hydrogen or $C_1$-$C_4$ alkyl; or the group;

is replaced by a heterocyclic radical bound to the carbon atom through the nitrogen atom and optionally containing another heteroatom, preferably selected from O, S, N;

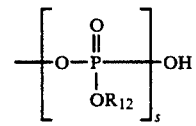

wherein $R_{12}$ is hydrogen or $C_1$-$C_8$ alkyl and s is an integer comprised between 1 and 3;

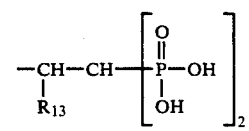

wherein $R_{13}$ is hydrogen or hydroxyl;

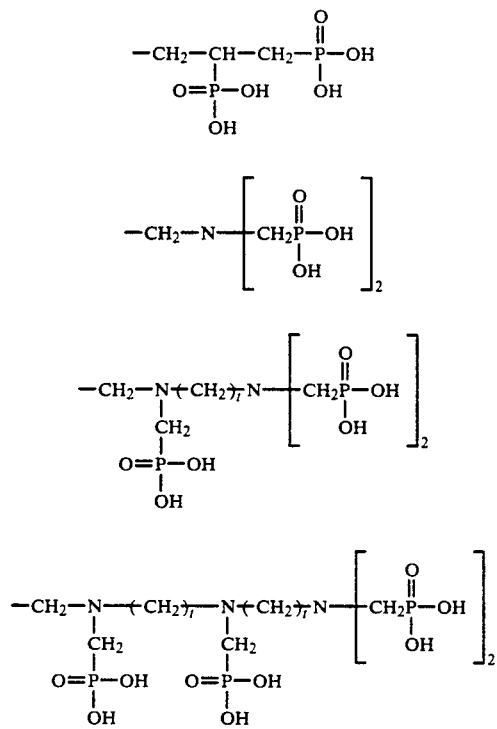

wherein t is an integer comprised between 2 and 6; or $R_6$ and $R_7$ together may form a cyclic structure of the formula:

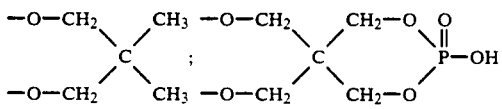

Examples of radicals from R to $R_5$ comprised in the formula (I) are: methyl; ethyl; propyl; isopropyl; n-butyl; isobutyl; tert butyl; n-pentyl isopentyl; n-hexyl; tert hexyl; n-octyl, tert -octyl; decyl; dodecyl; octadecyl; ethenyl; propenyl; butenyl; isobutenyl; hexenyl; octenyl; cyclohexyl; propylcyclohexyl; butylcyclohexyl; decylcyclohexyl; hydroxycyclohexyl; hydroxyethylcyclohexyl; 2-hydroxyethyl; 2-hydroxypropyl; 3-hydroxypropyl; 3-hydroxybutyl; 4-hydroxybutyl; 3-hydroxypentyl; 5-hydroxypentyl; 6-hydroxyhexyl; 3-hydroxy-2,5-dimethylhexyl; 7-hydroxyheptyl; 7-hydroxyoctyl; 2-methoxyethyl; 2-methoxypropyl; 3-methoxypropyl; 4-methoxybutyl; 6-methoxyhexyl; 7-methoxyheptyl; 7-methoxyoctyl; 2-ethoxyethyl; 3-ethoxypropyl; 4-ethoxybutyl; 4-isobutoxybutyl; 5-propoxypentyl; 2-cyclohexyloxyethyl; 2-ethenyloxyethyl; 2-(N,N-dimethylamino)ethyl; 3-(N,N-dimethylamino)propyl; 4-(N,N-dimethylamino)butyl; 5-(N,N-dimethylamino)pentyl; 5-(N,N-diisopropylamino)pentyl; 3-(N-ethylamino)propyl; 4-(N-methylamino)butyl; 4-(N,N-dipropylamino)hexyl; 2-(N-ethenylamino)ethyl; 2-(N-cyclohexylamino)ethyl; 2-(N-2-hydroxyethylamino)ethyl; 2-(2-hydroxyethoxy)ethyl; 2-(2-methoxyethoxy)ethyl; 6-(N-propylamino)hexyl; etc.

Examples of heterocyclic radicals which may replace the groups:

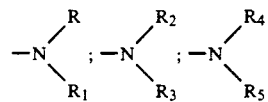

in the general formula (I) are: aziridine; pyrrolidine; piperidine; morpholine; thiomorpholine; piperazine; 4-methylpiperazine; 4-ethylpiperazine; 2-methylpiperazine; 2,5-dimethylpiperazine; 2,3,5,6-tetramethylpiperazine; 2,2,5,5-tetramethylpiperazine; 2-ethylpiperazine; 2,5-diethylpiperazine; etc.

Examples of heterocyclic radicals which may replace the group:

are: aziridine, pyrrolidine, piperidine; morpholine; thiomorpholine; piperazine; 4-methylpiperazine; 4-ethylpiperazine; etc.

Examples of acids containing phosphorus are: ipophosphorous acid; phosphorous acid; phosphoric acid; pirophosphoric acid; tripolyphosphoric acid; ethane-1,1,2-triphosphonic acid; 2-hydroxyethane-1,1,2-triphosphonic acid; 2-hydroxyethane-1,1,2-triphosphonic acid; propane-1,2,3-triphosphonic acid; isopropylphosphoric acid; n-butylphosphoric acid; di-n-butylphosphoric acid; diisopropylphosphoric acid; di-n-pentylphosphoric acid; isoctylphosphoric acid; hexylphosphoric acid; 2-ethylhexylphosphoric acid; methylphosphonic acid; ethylphosphonic acid; n-propylphosphonic acid; n-butylphosphonic acid; aminomethylphosphonic acid; phenylphosphoric acid; phenylphosphonic acid; phenylphosphinic acid; di-n-butylpyrophosphoric acid; di(2-ethylhexyl)pyrophosphoric acid; octylphenylphosphoric acid; 2-methylbenzylphosphonic acid; 1-aminoethane-1,1-diphosphonic acid; 1-hydroxyethane-1,1-diphosphonic acid; 1-hydroxydodecane-1,1-diphosphonic acid; 1-(N-methylamino)ethane-1,1-diphosphonic acid; N,N-dimethylaminomethane-1,1-diphosphonic acid; N-butylaminomethane-1,1-diphosphonic acid; phosphonoacetic acid; 2-phosphonopropionic acid; 3-phosphonopropionic acid; 2-phosphonobutyric acid; 4-phosphonobutyric acid; 2-hydroxy-5,5-dimethyl-2-oxo-1,3,2-dioxophosphorinane acid; 3,9-dihydroxy-2,4,8,10-tetraoxo-3,9-diphosphaspiro[5,5]undecane3,9dioxide; aminotris(methylenphosphonic) acid; ethylendiaminotetra (methylenphosphonic) acid; hexamethylendiaminotetra(methylenphosphonic)acid; diethylentriaminopenta(methylenphosphonic) acid; etc.

Specific compounds comprised in the formula (I) are reported in examples after the present description.

Saline compounds of the general formula (I) can be synthetized by reacting, in the presence of a suitable solvent (such as water, methyl alcohol, ethyl alcohol, acetonitrile, etc.) at temperatures comprised between 0° C. and the boiling point of the used solvent, n mols of a derivative of the 2,4,6-triamino-1,3,5-triazine of the general formula (II):

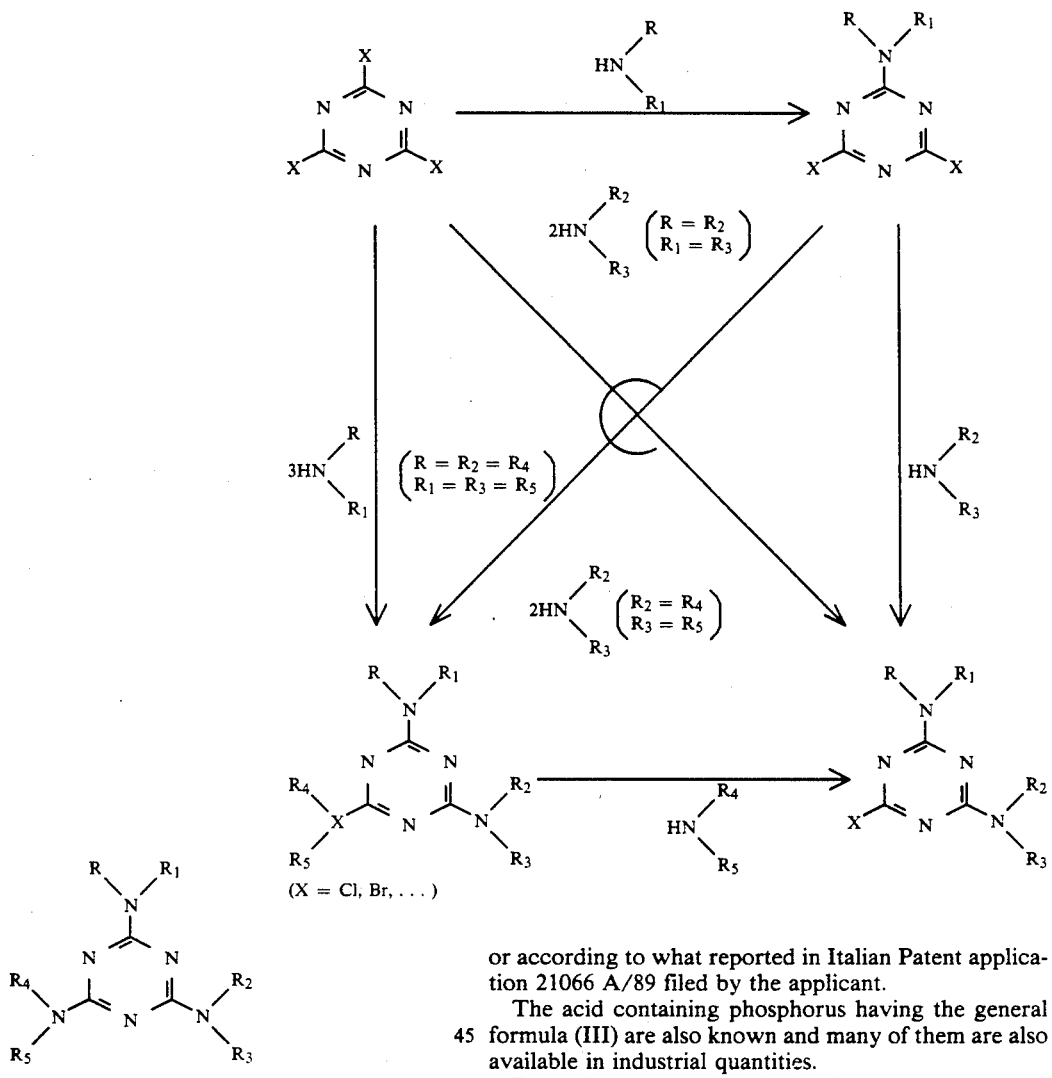

wherein n and the substituents from R to $R_5$ have the previously specified meaning, with one mol of an acid containing phosphorus of the general formula (III):

$$HO-\underset{R_6}{\underset{|}{\overset{O}{\overset{\|}{P}}}}-R_7 \qquad (III)$$

wherein $R_6$ and $R_7$ have the previously indicated meaning, or without solvent and with an excess of the acid containing the phosphorus, when this last can act as solvent, at temperatures comprised between 0° and 150° C.

The saline product thus formed can be easily separated from the reaction mass by filtration or by distilling the solvent.

Generally products of the general formula (I) are obtained, of good quality in form of white crystalline powder, useable in self-extinguishing polymeric compositions without further purifications.

Many of the intermediates of the general formula (II) are known; however, they can be easily synthetized according to the hereinafter schematized general method:

or according to what reported in Italian Patent application 21066 A/89 filed by the applicant.

The acid containing phosphorus having the general formula (III) are also known and many of them are also available in industrial quantities.

Examples reported hereinafter illustrate the characteristics of the present invention without limiting them.

Salification reactions between the intermediates of the general formula (I) and the acids containing phosphorus of the general formula (III) are confirmed by the IR spectroscopic analysis carried on a IR Perkin Elmer 580 B grid spectrophotometer.

In fact it has been observed that a very good reference signal consists of the band relating to the deformation out the plane of the triazinic ring: this band is placed at about 830-800 cm$^{-1}$ for the undisturbed ring, whilst it is placed at 795-760 cm$^{-1}$ for the ring salified on amino groups.

EXAMPLE 1

Into a 3 liters reactor, equipped with agitator, thermometer, dropping funnel, reflux cooler and heating bath, there are introduced: 184.5 g of the chloride of cyanuric acid and 800 cc of acetone.

The whole is agitated while heating to 40° C. until a solution is obtained; thereafter within 1 h and 30 minutes, while keeping the temperature at 40° C., 284 g of a 30% by weight solution of ammonia are added. The whole is then heated to 45° C. and is kept for 4 hours at this temperature.

After cooling, the formed product is filtered off and is washed with water on the filter. After drying in oven at 50°-60° C. under vacuum, 115 g of the intermediate (IV):

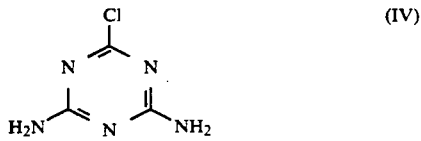

are obtained in form of infusible, white crystalline powder, having a chlorine content equal to 24.1% (theor. 24.36%).

The structure of this compound has been further confirmed by IR spectroscopic analysis.

Into a 1 liter reactor equipped with agitator, thermometer, funnel, reflux cooler and heating bath, there are introduced 72.8 g of the intermediate (IV), 350 g of water and thereafter, under agitation, 44 g of piperidine.

The mixture is heated to boiling and is kept under reflux for 4 hours.

Thereafter, the whole is further kept under reflux for 8 hours while adding in portions 20 g of sodium hydroxide in 50 g of water, in order to keep the pH comprised between 7 and 8.

After cooling at room temperature, the formed product is filtered and washed on the filter with water.

After drying in oven at 60° C. under vacuum, 90 g of 2,4-diamino-6-piperidino-1,3,5-triazine are obtained in form of a white crystalline powder, m.p.=215°-217° C. (m.p.=melting point).

Into the same 1 liter reactor there are introduced 77.6 g of 2,4-diamino-6-piperidino-1,3,5-triazine, 400 ml of water and, while agitating, 48.4 g of a 85% by weight phosphoric acid.

The mixture is heated to 80° C. and is kept at this temperature for 4 hours.

After cooling to 10° C., the formed product is filtered and washed on the filter with water.

After drying in oven at 100° C., 96 g of the product:

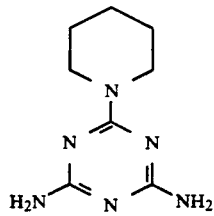

are obtained, in form of crystalline powder; m.p=228°-230° C. and phosphorus content equal to 10.52% (theor. 10.61%).

EXAMPLE 2

Into a 0.5 liter reactor, equipped as described in example 1, there are introduced 49.0 g of the intermediate (IV), 150 ml of water and 26.2 g of 2-methoxyethylamine.

The mass is heated to boiling and is kept under reflux for 4 hours.

Thereafter, a solution consisting of 14 g of sodium hydroxide in 50 ml of water is added within 20 minutes.

After having further agitated for 30 minutes, the distillation of water begins; the residual mass is then treated with three portions, each of 100 ml, of acetonitrile to extract the organic product.

By subsequent distillation of the solvent, 52.5 g of 2,4-diamino-6-(2-methoxyethyl)amino-1,3,5-triazine are obtained as white powder (m.p.=166°-169° C.).

Into the same 1 liter reactor of the example 1, there are introduced 52.5 g of 2,4-diamino-6-(2-methoxyethyl)amino-1,3,5-triazine, 600 ml of acetonitrile and, while agitating, 34.5 g of a 85% by weight phosphoric acid.

The whole is heated to boiling and kept under reflux for 4 hours.

After cooling to room temperature, the product formed is filtered and washed on the filter with acetonitrile.

After drying in oven at 100° C., 78 g of the product:

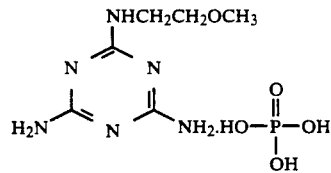

are obtained in form of white crystalline powder having m.p.=186°-188° C. and content of phosphorus equal to 11.0% (theor. 10.98%).

EXAMPLE 3

Into the same 1 liter reactor described in example 1, there are introduced 91 g of the intermediate (IV), 240 ml of toluene and 110 g of morpholine.

The mixture is heated to 65°-70° C. and is kept at this temperature for 2 hours; thereafter, it is heated to boiling and kept under reflux for 1 hour.

The mixture is allowed to cool to room temperature; thereafter, the product formed is separated by filtration. The cake is abundantly washed with water and, after drying, 92 g of 2,4-diamino-6-morpholino-1,3,5-triazine are obtained in form of a white crystalline powder having m.p.=248°-250° C.

Into a 0.5 liter reactor equipped as described in example 1, there are introduced 39.9 g of 2,4-diamino-6-morpholine-1,3,5-triazine, 250 ml of acetonitrile and, while agitating, 24.2 g of a 85% by weight phosphoric acid.

The mixture is heated to boiling and is kept under reflux for 8 hours.

Then, by working as described in example 2, 57 g of the product:

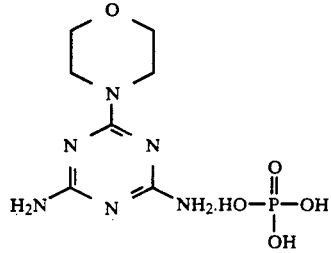

in form of white crystalline powder having m.p.=259°–252° C. and phosphorus content equal to 10.5% (theor. 10.54%) are obtained.

EXAMPLE 4

Into a 1 liter reactor equipped as described in example 1, there are introduced 72.8 g of the intermediate (IV), 250 ml of water and, while agitating, 104 g of thiomorpholine.

The mass is heated to boiling and is kept under reflux for 8 hours.

The whole is cooled to room temperature, the product formed is filtered and the cake is washed with water.

After drying in oven at 100° C., 90.2 g of 2,4-diamino-6-thiomorpholino-1,3,5-triazine are obtained in form of a white crystalline powder; m.p.=237°–239° C.

Into the same 1 liter reactor there are introduced 41.4 g of 2,4-diamino-6-thiomorpholino-1,3,5-triazine, 300 ml of water and, while agitating, 32.5 g of phenylphosphonic acid.

The mixture is heated to 80° C. and is kept at this temperature for 6 hours.

After cooling to room temperature, the product formed is filtered and washed on the filter with a little amount of water.

After drying in oven at 100° C., 64.7 g of the product:

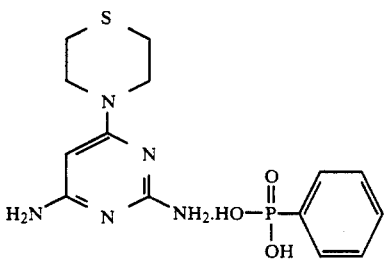

are obtained in form of a white powder; m.p. 265°–269° C.; phosphorus content =8.14% (theor. 8.38%).

EXAMPLE 5

Into the same 3 liters reactor of example 1, there are introduced 136 g of the intermediate (IV) and 800 ml of xylene.

The suspension is heated to 120° C. and within 1 h, 302 g of the ethyl ester of the N-piperazinecarboxylic acid are added.

The whole is kept at 125°–130° C. for 2 hours, then is cooled to room temperature and the product formed is filtered, while washing the cake at first with xylene and then abundantly with water.

After drying in oven at 100° C., 230 g of the intermediate (V):

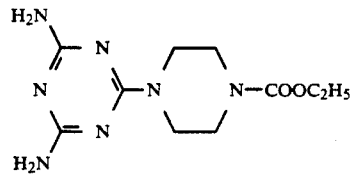

are obtained in form of white crystalline powder; m.p.=210°–215° C.

Furthermore, the structure of this intermediate has been confirmed by NMR analysis.

Into the same reactor there are introduced 1000 ml of acetic acid, 620 g of acetic solution of a 33% by weight hydrobromic acid and 120 g of the intermediate (V).

The whole is heated to 95° C. and is kept under agitation at this temperature for 6 hours.

Subsequently, the whole is cooled to room temperature and the product formed is filtered and washed on the filter with acetic acid.

The squeezed cake is then treated in a 2 liter glass with 500 ml of water and added, under agitation, with a 50% by weight sodium hydroxide solution until the pH 11 is reached.

The whole is agitated for further 1 hour and then the product formed is filtered and washed abundantly on the filter with water.

After drying in oven at 100° C., 60 g of 2,4-diamino-6-piperazino-1,3,5-triazine are obtained in form of white powder; m.p.=262°–268° C.

Into the same 1 liter reactor of example 1, however now equipped with a cooling bath, there are introduced 106.4 g of tetrasodium pyrophosphate and 600 ml of water.

The mixture is cooled to 5° C. from the outside and thereafter 158 g of a 37% by weight hydrochloric acid are added thus obtaining a solution.

The solution, always at 5° C., is added with 78 g of 2,4-diamino-6-piperazino-1,3,5-triazine.

The whole is kept under agitation for 2 hours at the same temperature of 5° C.; thereafter, it is heated to 10° C. and is kept at this new temperature for 3 hours.

After having cooled to 2° C., the product formed is separated by filtration and the cake is washed on the filter with a little amount of cold water.

After drying in oven at 100° C., 102 g of the product;

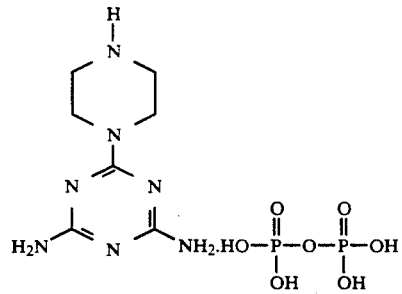

are obtained in form of white crystalline powder; m.p. =295°–298° C.; phosphorus content equal to 16.8% (theor. 16.61%).

EXAMPLE 6

Into the same 3 liters reactor described in example 1, but equipped at the starting with a cooler bath, there are introduced 184.5 g of cyanuric acid chloride and 1300 ml of methylene chloride.

While cooling from the outside, 87.2 g of morpholine and 40 g of sodium hydroxide dissolved in 150 g of water are introduced into the reactor at the same time, within 3 hours, while keeping the pH comprised between 5 and 7 and the temperature between 0° and 3° C.

The whole is further kept at the temperature of from 0° to 3° C. for 3 hours and then the aqueous phase is separated.

By distillation of the methylene chloride, 230 g of the intermediate (VI):

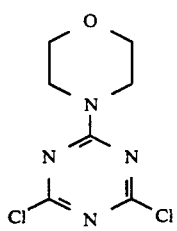
(VI)

are obtained in form of white crystalline powder; m.p.=155-157; titre higher than 98% (determined by gas chromatography); chlorine content equal to 29.87% (theor. 30.21%).

Into a 0.5 liter reactor, equipped as described in example 1, there are introduced 100 g of a 30% by weight ammonia solution, 100 ml of water and 70.5 g of the intermediate (VI).

The mixture is heated to 50° C. and is kept at this temperature for 7 hours; after having allowed the mixture to cool to room temperature, the product obtained is filtered and washed with water.

By drying the cake, 58 g of the intermediate (VII):

(VII)

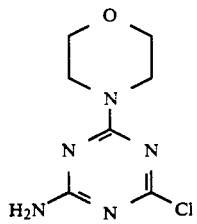

are obtained in form of white crystalline powder; m.p.=189°-191° C. and chlorine content 16.28% (theor. 16.47%).

The structure of compounds (VI) and (VII) has been confirmed by IR spectroscopic analysis.

Into the same apparatus above described there are introduced 58 g of the intermediate (VII) and 300 g of water and thereafter, under agitation, 18 g of 2-aminoethanol.

The whole is heated to boiling and is kept under reflux for 3 hours.

Thereafter, the mixture is further kept under reflux for 3 hours while adding in portions 11.8 g of sodium hydroxide in 50 g of water, to maintain the pH comprised between 7 and 8.

The mass is cooled, the product obtained is filtered and the cake is washed with water.

After drying 58 g of 2-amino-4-(2-hydroxyethyl-)amino-6-morpholino-1,3,5-triazine, in form of white powder are obtained; m.p.=159°-161° C.

Into a 1 liter reactor equipped as in example 1 there are introduced 328 g of phosphorous acid and 82 g of acetonitrile.

The reaction mixture is gradually heated, within 6 hours, up to 160° C.

A white crystalline product is formed.

Subsequently, the mass is cooled to 80° C. and is added under a good agitation with 500 ml of water; thereafter it is allowed to cool to room temperature.

The product formed is separated by filtration and is washed on the filter with a little amount of water.

After drying of the cake, 290 g of 1-amino ethane-1,1-diphosphonic acid are obtained, in form of white crystalline powder; m.p.=265°-270° C. (with decomposition); phosphorus content equal to 29.4% (theor. 30.24%).

Into a 0.5 liter reactor, equipped as in example 1, there are introduced 200 ml of water, 36 g of 2-amino-4-(2-hydroxyethyl)amino-6-morpholino-1,3,5-triazine and 16 g of 1-aminoethane-1,1-diphosphonic acid.

The mass is heated to 80° C. and is maintained at this temperature for 1 hour, then the distillation of the solvent is begun.

By drying in oven at 100° C. the solid which remains after the distillation, 51.6 g of the product:

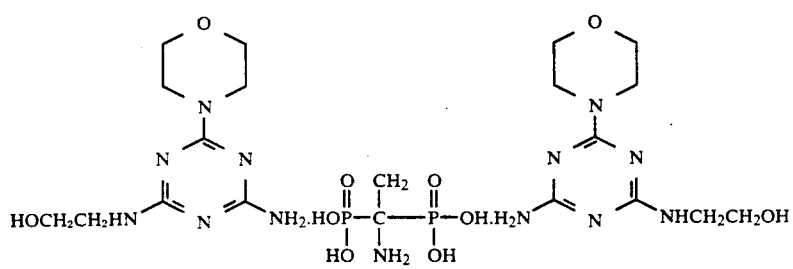

are obtained in form of white crystalline powder; m.p.=144°-148° C. and phosphorus content 8.8% (theor. 9.04%).

EXAMPLE 7

Into a 2 liters reactor, equipped as in the preceding examples, there are introduced 184.4 g of cyanuric acid chloride and 800 ml of methylene chloride.

By cooling from outside, the solution kept at 4°-5° C. is added within 2 hours with 174 g of morpholine dissolved in 150 ml of water.

The temperature is allowed to raise to 10° C. and, while keeping it between 10° and 20° C., a solution consisting of 80 g of sodium hydroxide in 200 g of water is added within 4 hours. The whole is still kept at the temperature of 20° C. for 2 hours and thereafter the aqueous phase is removed.

By distilling the methylene chloride, 270 g of the intermediate (VIII):

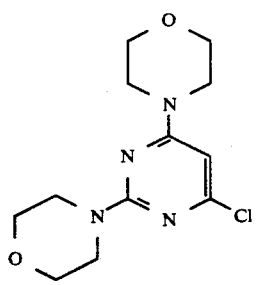

(VIII)

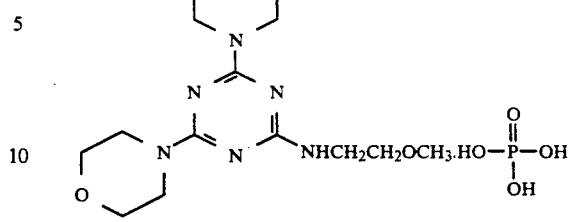

are obtained in form of white crystalline powder; m.p.=172°-174° C.; chlorine content equal to 12.31% (theor. 12.43%).

Furthermore, the structure of this intermediate has been confirmed by NMR analysis.

Into a 1 liter reactor, equipped as described in example 1, there are introduced 500 ml of water, 57.1 g of the intermediate (VIII) and, under agitation, 15.0 g of 2-methoxyethylamine.

The whole is heated to boiling and is maintained under reflux for 2 hours; thereafter, within about 1 hour, 8.0 g of sodium hydroxide dissolved in 80 ml of water are added.

After having maintained under reflux for further 4 hours, the whole is cooled to room temperature and the product formed is extracted with 2 portions of methylene chloride (each portion being of 200 ml).

By subsequent distillation of the solvent and drying in oven of the residue of the distillation, 59.2 g of 2,4-dimorpholino-6-(2-methoxyethyl)amino-1,3,5-triazine are obtained; m.p.=120°-122° C.

Into a 0.5 liter reactor, equipped as in example 1, there are introduced 48.6 g of 2,4-dimorpholino-6-(2-methoxyethyl)amino-1,3,5-triazino, 300 cc of acetonitrile and, under agitation, 17.4 g of a 85% by weight phosphoric acid.

The mixture is heated to boiling and is maintained under reflux for 4 hours.

The whole is then cooled to room temperature and the product formed is filtered and washed on the filter with a little amount of acetonitrile.

After drying of the cake in oven at 100° C., 63 g of the product:

are obtained in form of white crystalline powder; m.p.=179°-182° C.; phosphorus content equal to 7.46% (theor. 7.33%).

EXAMPLE 8

Into a 0.5 liter reactor, equipped as in example 1, there are introduced 39.2 g of 2,4-diamino-6-morpholino-1,3,5-triazine (prepared as described in example 3), 300 ml of ethyl alcohol and, under agitation, 17.2 g of phosphorous acid.

The mixture is maintained under agitation at room temperature for 8 hours; thereafter, the product formed is filtered and washed on the filter with a little amount of solvent.

By drying the cake in oven at 100° C., 55 g of the product:

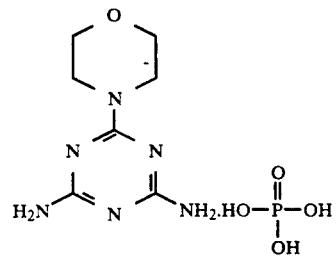

are obtained in form of white crystalline powder; m.p.=240-244; content of phosphorus equal to 11.0% (theor. 11.13%).

EXAMPLES 9-37

By working under conditions analogous to those described in examples from 1 to 8, the saline products of general formula (I) listed in Table 1 are prepared

TABLE 1

| Ex. No. | R—N—R$_1$ | R$_2$—N—R$_3$ | R$_4$—N—R$_5$ | $\underset{R_6}{\overset{O}{\underset{\|}{HO-P-R_7}}}$ | n | m.p. (°C.) | phosphorus % found | phosphorus % calculated |
|---|---|---|---|---|---|---|---|---|
| 9 | morpholino | H  H | H | H$_3$PO$_4$ | 1 | 242–244 | 8,50 | 8,52 |
| 10 | morpholino | CH$_2$CH$_2$OH  H | H | H$_3$PO$_4$ | 1 | 185–189 | 8,94 | 9,16 |
| 11 | morpholino | H  H | H | HO–P(=O)(OH)–O–P(=O)(OH)–OH | 2 | 149–151 | 10,76 | 10,87 |
| 12 | piperazino (NH) | H  H | H | CH$_3$–C(NH$_2$)(P(=O)(OH)$_2$)$_2$ | 1 | 225–229 | 15,25 | 15,5 |
| 13 | morpholino | H  H | H | CH$_3$–C(NH$_2$)(P(=O)(OH)$_2$)$_2$ | 1 | 230–235 | 15,24 | 15,45 |
| 14 | morpholino | H  H | H | CH$_3$–C(NH$_2$)(P(=O)(OH)$_2$)$_2$ | 2 | 205–210 | 10,21 | 10,37 |
| 15 | morpholino | H  H | H | cyclic phosphate (OCH$_2$)$_2$C(CH$_3$)$_2$–P(=O)OH | 1 | 268–270 | 8,17 | 8,55 |
| 16 | morpholino | morpholino | CH$_2$CH$_2$OH  H | H$_3$PO$_4$ | 1 | 180–182 | 8,45 | 7,59 |

TABLE 1-continued

| Ex. No. | R—N—R$_1$ | R$_2$—N—R$_3$ | R$_4$—N—R$_5$ | $HO-\overset{\overset{O}{\|}}{\underset{R_6}{P}}-R_7$ | n | m.p. (°C.) | phosphorus % found | phosphorus % calculated |
|---|---|---|---|---|---|---|---|---|
| 17 | morpholine | t-C$_4$H$_9$ | H H | H$_3$PO$_4$ | 1 | 173-176 | 8,69 | 8,86 |
| 18 | morpholine | CH$_2$—CH=CH$_2$ | H H | $HO-\overset{O}{\underset{OH}{P}}-O-\overset{O}{\underset{OH}{P}}-OH$ | 2 | 136-139 | 9,37 | 9,53 |
| 19 | (CH$_2$)$_2$OCH=CH$_2$ CH$_3$ | H | H H | H$_3$PO$_4$ | 1 | 162-165 | 9,90 | 10,06 |
| 20 | CH$_2$CH$_2$CH$_2$N-morpholine H | H | H H | H$_3$PO$_3$ | 1 | 189-191 | 9,16 | 9,25 |
| 21 | morpholine | H | H H | $\{HO-\overset{O}{\underset{OH}{P}}-O-nC_4H_9$ 40%, $HO-\overset{O}{\underset{O-nC_4H_9}{P}}-O-nC_4H_9$ 60%$\}$ | 1 | 152-182 | 8,04 | 8,12 |
| 22 | morpholine | H | H H | $HO-\overset{O}{\underset{OH}{P}}-O-\overset{O}{\underset{OH}{P}}-O-\overset{O}{\underset{OH}{P}}-OH$ | 3 | 144-148 | 10,78 | 11,0 |
| 23 | (CH$_2$)$_2$O(CH$_2$)$_2$OH H | (CH$_2$)$_2$O(CH$_2$)$_2$OH | H H | H$_3$PO$_4$ | 1 | 149-152 | 7,48 | 7,75 |
| 24 | morpholine | H | H H | $HO-\overset{O}{\underset{OH}{P}}-\overset{CH_3}{\underset{OH}{C}}-\overset{O}{\underset{OH}{P}}-OH$ | 2 | 179-182 | 10,18 | 10,35 |

TABLE 1-continued

| Ex. No. | R—N—R$_1$ | R$_2$—N—R$_3$ | | R$_4$—N—R$_5$ | $\overset{O}{\underset{R_6}{HO-P-R_7}}$ | n | m.p. (°C) | phosphorus % found | calculated |
|---|---|---|---|---|---|---|---|---|---|
| 25 | morpholine | H | H | H | phenyl-P(O)(OH)$_2$ | 1 | 257–262 | 8,12 | 8,74 |
| 26 | CH$_2$CH$_2$OH, cyclohexyl | H | H | H | H$_3$PO$_4$ | 1 | 141–144 | 8,80 | 8,86 |
| 27 | morpholine | H | H | H | $N(CH_2P(O)(OH)OH)_3$ | 3 | 136–142 | 10,32 | 10,48 |
| 28 | morpholine | morpholine | H | CH$_2$CH$_2$OH, CH$_3$ | H$_3$PO$_4$ | 1 | 172–174 | 7,62 | 7,34 |
| 29 | thiomorpholine | H | H | H | $(HO)(O)P-CH_2CH(P(O)(OH)OH))_2$ | 3 | 192–197 | 9,87 | 10,26 |
| 30 | CH$_2$CH$_2$OH, CH$_2$CH$_2$OH | H | H | H | C$_{11}$H$_{23}$C(P(O)(OH)$_2$)$_2$OH | 2 | 139–143 | 7,64 | 8,01 |
| 31 | piperazine | H | H | H | H$_3$PO$_4$ | 0,5 | 200–205 | 15,82 | 15,86 |

TABLE 1-continued

| Ex. No. | R—N—R$_1$ | R$_2$—N—R$_3$ | R$_4$—N—R$_5$ | $HO-\overset{\overset{O}{\|}}{P}-R_7$ $R_6$ | n | m.p. (°C.) | phosphorus % found | calculated |
|---|---|---|---|---|---|---|---|---|
| 32 | morpholine | t-C$_8$H$_{17}$ H | H H | H$_3$PO$_4$ | 1 | 141–145 | 7,55 | 7,63 |
| 33 | morpholine | H | H H | pentaerythritol bis-phosphate structure | 2 | 262–267 | 9,35 | 9,5 |
| 34 | morpholine | H | H H | $\{(CH_2)_2N[CH_2\overset{\overset{O}{\|}}{P}(OH)_2]_2\}_2N-CH_2\overset{\overset{O}{\|}}{P}(OH)_2$ | 5 | 185–190 | 9,78 | 9,98 |
| 35 | morpholine | CH$_2$CH$_2$OH | H H | phenyl-H-phosphinic acid | 1 | 174–177 | 7,86 | 8,11 |
| 36 | (CH$_2$)$_5$OH | H | H H | H$_3$PO$_4$ | 1 | 186–189 | 9,78 | 10,0 |

EXAMPLE 37

60 g of isotactic polypropylene in flakes having a Melt Flow Index equal to 12 and an insoluble fraction in boiling n-heptane equal to 96% by weight, 39 g of the product of example 3, 0.67 g of dilaurylthiopropionate and 0.33 g of pentaerythritol tetra [3-(3,5-diterbutyl-4-hydroxyphenyl)propionate], are mixed and molded in a MOORE plate press, by working for 7 minutes under a 40 kg/cm² pressure.

Samples in form of plates having a thickness of about 3 mm are obtained, on which the self-extinguishing level is determined by measuring the oxygen index (L.O.I. according to the ASTM D-2863/77) in a STANTON REDCROFT apparatus, and applying the "Vertical Burning Test" which allows to classify the material at three levels 94 V-0, 94 V-1 and 94 V-2, according to UL 94 published by "Underwriters Laboratories"- USA).

The following results are obtained:
L.O.I.=35.4
UL 94: Class V-0

We claim:

1. Salts of triazinic compounds with oxygenated acids of phosphorus, of the formula (I)

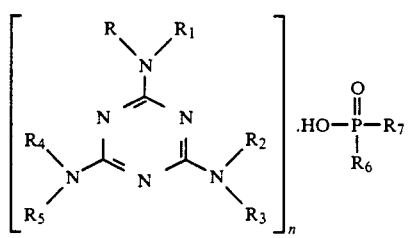

wherein at least one of the radicals R to $R_5$ is

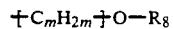

or

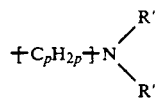

m = an integer between 2 and 8;

p = an integer between 2 and 6; $R_8$ = is selected from the group consisting of a hydrogen atom, $C_1$-$C_8$ alkyl; $C_2$-$C_6$ alkenyl; and $[C_qH_{2q}]$—O—$R_9$, wherein q is an integer between 1 and 4 and $R_9$ is hydrogen or $C_1$-$C_4$ alkyl; $C_6$-$C_{12}$ cycloalkyl or alkylcycloalkyl;

radicals R' are the same or different, and are selected from the group consisting of a hydrogen atom, $C_1$-$C_8$ alkyl; $C_2$-$C_6$ alkenyl; $C_6$-$C_{12}$ cycloalkyl or alkylcycloalkyl; $C_1$-$C_4$ hydroxyalkyl, provided that radicals $R_6$ and $R_7$, hereinafter specified, are respectively different from H and OH; or the group:

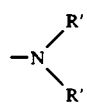

is replaced by a heterocyclic radical bound to the alkyl chain through the nitrogen atom selected from the group consisting of aziridine; pirrolidine; piperidine; morpholine; thiomorpholine; piperazine; 4-methylpiperazine; and 4-ethylpiperazine or in the formula (I) at least one of the groups:

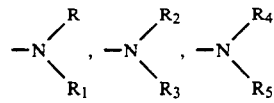

is replaced by a heterocyclic radical bound to the triazine ring through the nitrogen atom said heterocyclic radical selected from the group consisting of aziridine; pirrolidine; piperidine, morpholine; thiomorpholine; piperazine; 4-methylpiperazine; 4-ethylpiperazine; 2-methylpiperazine; 2,5-dimethylpiperazine; 2,3,5,6-tetramethylpiperazine; 2,2,5,5-tetramethylpiperazine; 2-ethylpiperazine; 2,5-diethylpiperazine the other radicals from R to $R_5$ are the same or different and have the above mentioned meaning or are selected from the group consisting of a hydrogen atom; $C_1$-$C_{18}$ alkyl; $C_2$-$C_8$ alkenyl; $C_6$-$C_{16}$ cycloalkyl or alkylcycloalkyl, optionally substituted by a hydroxy or $C_1$-$C_4$ hydroxyalkyl;

n is 0.5 to 6;

$R_6$ is selected from the group consisting of a hydrogen atom; OH; O—$C_1$-$C_8$ alkyl; O-phenyl, optionally substituted by a $C_1$-$C_8$ alkyl; aralkyl, optionally substituted by a $C_1$-$C_4$ alkyl; $C_1$-$C_4$ alkyl, optionally substituted by a carboxylic group; aryl;

$R_7$ is hydrogen; OH; —O—$C_1$-$C_8$ alkyl; O-phenyl; $C_1$-$C_4$ alkyl; aryl;

$R_7$ is:

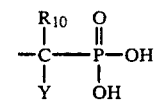

wherein $R_{10}$ is a hydrogen atom or $C_1$-$C_{12}$ alkyl; and Y is OH or $R_{10}$;

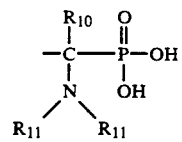

wherein $R_{10}$ has the previously defined meaning and radicals $R_{11}$ are the same or different and are a hydrogen atom or $C_1$-$C_4$ alkyl;

or the group:

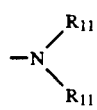

is replaced by a heterocyclic radical bound to the carbon atom through the nitrogen atom and optionally containing a second heteroatom selected from the group consisting of S, O and N;

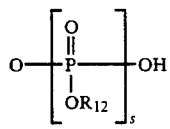

wherein $R_{12}$ is a hydrogen atom or $C_1$-$C_8$ alkyl and s is an integer between 1 and 3;

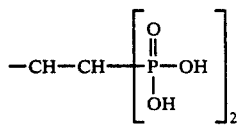

wherein $R_{13}$ is hydrogen or hydroxyl;

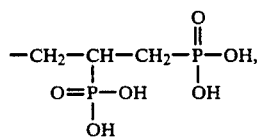

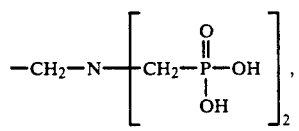

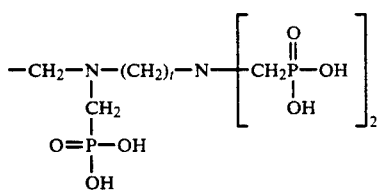

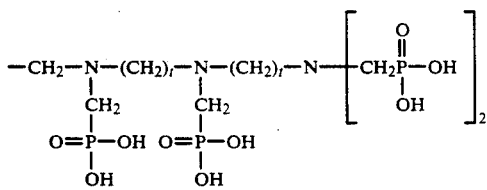

wherein t is an integer between 2 and 6; or $R_6$ and $R_7$ together may form a cyclic structure of the formula;

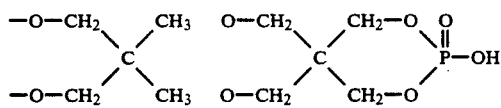

2. Salts of triazinic compounds with oxygenated acids of phosphorus according claim 1 wherein the acid of the phosphorus is selected from the group consisting of: hypophosphorous acid; phosphorous acid; phosphoric acid; pirophosphoric acid; tripolyposphoric acid; ethane-1,1,2-triphosphonic acid; 2-hydroxyethane-1,1,2-triphosphonic acid; propane-1,2,3-triphosphonic acid; isopropylphosphoric acid; n-butylphosphoric acid; di-n-butylphosphoric acid; di-isopropylphosphoric acid; di-n-pentylphosphoric acid; isooctylphosphoric acid; ethylphosphoric acid; 2-ethylhexylphosphoric acid; methylphosphonic acid; ethylphosphonic acid; n-propylphosphonic acid; n-butylphosphonic acid; aminomethylphosphonic acid; phenylphosphoric acid; phenylphosphonic acid; phenylphosphinic acid; di-n-butylpirophoric acid; di(2-ethylhexyl)pirophosphoric acid; octylphenylphosphoric acid; 2-methylbenzylphosphonic acid; 1-aminoethane-1,1-diphosphonic acid; 1-hydroxyethane-1,1-diphosphonic acid; 1-hydroxydodecane-1,1-diphosphonic acid; 1-(N-methylamino)ethane-1,1-diphosphonic acid; N,N-dimethylaminomethane-1,1-diphosphonic acid; N-butylaminomethane-1,1-diphosphonic acid; phosphonacetic acid; 2-phosphonopropionic acid; 3-phosphonopropionic acid; 2-phosphonobutyric acid; 4-phosphonobutyric acid; 2-hydroxy-5,5dimethyl-2-oxo-1,3,2-dioxophosphorinane; 3,9-dihydroxy-2,4,8,10-tetraoxo-3,9-diphosphaspiro[5,5]undecane-3,9-dioxide; aminotris(methylenphosphonic) acid; ethylendiaminotetra (methylenphosphonic) acid; hexamethyldiaminotetra (methylenphosphonic) acid; diethylentriaminopenta (methylenphosphonic) acid.

3. Salts of triazinic compounds with oxygenated acids of phosphorus according to claim 1 wherein the group:

is replaced by a heterocyclic radical selected from the group consisting of: aziridine; pirrolidine; piperidine; morpholine; thiomorpholine; piperazine; 4-methylpiperazine; and 4-ethylpiperazine.

4. Salts of triazinic compounds with oxygenated acids of phosphorus according claim 1 wherein the acid of the phosphorus is selected form the group consisting of: hypophosphorous acid; phosphorous acid; phosphoric acid; pirophosphoric acid; tripolyposphoric acid; ethane-1,1,2-triphosphonic acid; 2-hydroxyethane-1,1,2-triphosphonic acid; propane-1,2,3-triphosphonic acid; isopropylphosphoric acid; n-butylphosphoric acid; di-n-butylphosphoric acid; diisopropylphosphoric acid; di-n-pentylphosphoric acid; isooctylphosphoric acid; ethylphosphoric acid; 2-ethylhexylphosphoric acid; methylphosphonic acid; ethylphosphonic acid; n-propylphosphonic acid; n-butylphosphonic acid; aminomethylphosphonic acid; phenylphosphoric acid; phenylphosphonic acid; phenylphosphinic acid; di-n-butylpirophoric acid; di(2-ethylhexyl)pirophosphoric acid; octylphenylphosphoric acid; 2-methylbenzylphosphonic acid; 1-aminoethane-1,1-diphosphonic acid; 1-hydroxyethane-1,1-diphosphonic acid; 1-hydroxydodecane-1,1-diphosphonic acid; 1-(N-methylamino)ethane-1,1-diphosphonic acid; N,N-dimethylaminomethane-1,1-diphosphonic acid; N-butylaminomethane-1,1-diphosphonic acid; phosphonacetic acid; 2-phosphonopropionic acid; 3-phosphonopropionic acid; 2-phosphonobutyric acid; 4-phosphonobutyric acid; 2-hydroxy-5,5-dimethyl-2-oxo-1,3,2-dioxophosphorinane; 3,9-dihydroxy-2,4,8,10-tetraoxo-3,9-diphosphaspiro[5,5] undecane-3,9-dioxide; aminotris(methylenphosphonic) acid; ethylendiaminotetra(methylenphosphonic) acid; hexamethyldiaminotetra (methylenphosphonic) acid; diethylentriaminopenta (methylenphosphonic) acid.

* * * * *